United States Patent [19]

Heilmann et al.

[11] Patent Number: 5,091,489
[45] Date of Patent: Feb. 25, 1992

[54] OLIGO (2-ALKENYL AZLACTONES)

[75] Inventors: Steven M. Heilmann; Dean M. Moren; Jerald K. Rasmussen; Larry R. Krepski; Sadanand V. Pathre, all of St. Paul, Minn.

[73] Assignee: Minnesota Mining and Manufacturing Company, St. Paul, Minn.

[21] Appl. No.: 734,925

[22] Filed: Jul. 24, 1991

Related U.S. Application Data

[62] Division of Ser. No. 602,100, Oct. 23, 1990.

[51] Int. Cl.$^5$ .................. C08F 4/20; C08F 126/06
[52] U.S. Cl. ........................... 526/90; 526/214; 526/238; 526/260
[58] Field of Search ............... 526/260, 90, 214; 548/228; 544/73

[56] References Cited

U.S. PATENT DOCUMENTS 4,304,705 12/1981 Heilmann et al. ............ 525/279 X

Primary Examiner—Joseph L. Schofer
Assistant Examiner—M. Nagumo
Attorney, Agent, or Firm—Gary L. Griswold; Walter N. Kirn; Lorraine R. Sherman

[57] ABSTRACT

This invention provides novel azlactone-functional oligomers of 2-alkenyl azlactones in which oligomerization has occurred predominantly via the 2-alkenyl group. Oligomerization of the 2-alkenyl group provides oligomers having 2 to 15 mer units with predominantly carbon-carbon backbone segments. Oligomerized in this fashion, the novel compositions possess azlactone groups which can be reacted with nucleophiles in the normal ring-opening sense. The oligomers are prepared by a novel process in which both Lewis and Bronsted acidic catalysts are effective. The reactive oligomers find utility as crosslinking agents for polymers containing azlactone-reactable nucleophilic groups.

7 Claims, 7 Drawing Sheets

OLIGO (2-ALKENYL AZLACTONES)

This is a division of application Ser. No. 07/602,100 filed Oct. 23, 1990.

FIELD OF THE INVENTION

This invention relates to a reactive oligomer obtained by the acid catalyzed oligomerization of 2-alkenyl azlactones. The novel reactive oligomers find utility as crosslinking agents in pressure sensitive adhesives.

BACKGROUND OF THE INVENTION

Addition polymerization reactions of vinyl monomers can involve anionic, free radical, or cationic intermediates. The reaction mechanism for polymerization is illustrated in the scheme below in which I represents an initiator; the asterisk signifies a negative charge, a free radical, or a positive charge; and Z represents hydrogen, halogen, or an organic group.

Initiation:

Propagation:

Termination

Distinct initiation, propagation, and termination phases of a polymerization constitute a so-called chain reaction when the termination reaction provides an active by-product (designated I'* above) capable of initiating another polymerization sequence in addition to inactive polymer.

Whether polymerization involves anionic, free radical, or cationic intermediates is largely determined by the nature of Z in the vinyl monomer. Although many vinyl monomers are efficiently polymerized by free radical initiation, most polymerize ionically, if at all, by only one kind of active center. Methyl acrylate (in which $Z=CO_2CH_3$), for example, polymerizes efficiently by radical and anionic initiation, but essentially not at all by cationic means. Generally speaking, Z groups which provide electronic and resonance stabilization by releasing electron density facilitate polymerization via cationic intermediates, while Z groups which withdraw electrons stabilize anionic intermediates.

That the azlactone group is electron withdrawing relative to hydrogen and 2-alkenyl azlactones (2-oxazolin-5-ones) possess 2-alkenyl groups which are electron deficient relative to ethylene are indicated by at least two factors. First of all, 2-vinyl-4,4-dimethylazlactone (VDM) can be effectively polymerized employing free radical techniques (cf. J. K.. Rasmussen, S. M. Heilmann, and L. R. Krepski, "Polyazlactones" in *Encyclopedia of Polymer Science and Engineering*, Volume 11, Second Edition, John Wiley & Sons, Inc.: New York, 1988, pp. 558-571). An indication of the electron supplying/withdrawing behavior of the azlactone group and the propensity of VDM to polymerize by ionic active centers can be obtained by examining free radical copolymerization with styrene. When this experiment was conducted in the above reference, the "e" value or measure of the polarity of the vinyl group in VDM was determined to be +0.65. By comparison with the e value for methyl acrylate of +0.64 (cf. R. Z. Greenley, "Q and e Values for Free Radical Copolymerization of Vinyl Monomers and Telogens" in *Polymer Handbook* edited by J. Brandrup and E. H. Immergut, Third Edition, John Wiley & Sons, Inc.: New York, 1989, II-267 to II-274), the azlactone heterocycle possesses approximately the same electron withdrawing capability as the carbomethoxy group and would be expected to stabilize anionic intermediates.

Another indication of the relative electron deficiency of the 2-alkenyl group in VDM can be obtained from its $^{13}$C-NMR spectrum. K. Hatada et al., *Makromol. Chem.*, 178, 2413-2419 (1977) have utilized the relative position of the resonance of the 1-carbon of a terminal olefin to successfully predict whether the olefin will polymerize by anionic or cationic initiation. Using the carbon disulfide $^{13}$C resonance as a reference signal (193.7 ppm relative to the more traditional tetramethylsilane reference), these workers observed that monomers with 1-carbon resonances of about 100 ppm upfield, i.e., to the right or at higher energy, from the carbon disulfide resonance polymerized by cationic intermediates. Monomers with 1-carbons resonating at about 70 ppm responded to anionic initiation. Since VDM exhibits a 1-carbon resonance at 64.7 ppm on this scale, one would predict that 2-alkenyl azlactones would respond to anionic but not to cationic polymerization techniques.

Reports exist of electron deficient olefins which oligomerize or polymerize in the presence of acid. Tomalia et al. (*Polymer J.*, 1980, 12, 661) motivated by the observation "that a variety of unidentified polymers, gels, or oligomeric syrups were readily formed by merely allowing 2-alkenyl-2-oxazolines to come in contact with Bronsted acids at room temperature" initially reported the oligomerization and polymerization of 2-isopropenyl-2-oxazoline (IPO). IPO is an electron deficient olefin as indicated by the e value of +0.34 for the 4,4-dimethyl derivative (*Polymer Handbook*, II-271) and a $^{13}$C-NMR 1-carbon resonance of 73 ppm upfield from the carbon disulfide resonance. They reported the formation of cyclic dimers in the presence of strong monoprotic Bronsted acids such as trifluoromethanesulfonic acid and low molecular weight ($\overline{M}_N=900$ to 2500) polymers when strong diprotic Bronsted acids such as sulfuric acid were utilized. These results are summarized in the Scheme below:

a = integer of 6 to 20

With the exception of the six-membered ring dimer, all proposed structures involve the oxazoline nitrogen as a main-chain atom resulting from Michael or 1,4-addition of the nitrogen to the enone-like system of the 2-isopropenyl-2-oxazolinium species followed by proton transfer from nitrogen to carbon.

Similarly, Saegusa et al. (*Polymer J.*, 1987, 19, 557) reported, based on the $^1$H-NMR spectrum, that 2-vinyloxazolinium fluorosulfonate, prepared from 2-vinyl-2-oxazoline and fluorosulfonic acid, provided a mixed polymer of predominantly monomer units in which nitrogen was present in the main-chain (80%) and a minor amount of vinyl polymerized units (20%).

Michael Units    Vinyl Units

SUMMARY OF THE INVENTION

Briefly, this invention provides an azlactone-functional oligomer having 2 to 15 units of which at least 30 mole percent are 2-alkenyl group polymerized units. The novel azlactone-functional oligomers of 2-alkenyl azlactones are the product of oligomerization which has occurred predominantly via the 2-alkenyl group. Oligomerization of the 2-alkenyl group provides oligomers with predominantly carbon-carbon backbone segments. Oligomerized in this fashion, the novel compositions possess azlactone groups which can be reacted with nucleophiles in the normal ring-opening sense.

In another aspect of the invention, the oligomers are prepared by a novel process in which both Lewis and Bronsted acidic catalysts are effective. The reactive oligomers find utility as crosslinking agents for polymers containing azlactone-reactable nucleophilic groups.

In contrast to the acid catalyzed oligomerization and polymerization of 2-alkenyl-2-oxazolines in which predominantly Michael units were formed, the 2-alkenyl azlactones (2-oxazolin-5-ones) of the invention yield oligomers containing predominantly vinyl units, i.e., carbon-carbon backbones.

In this application:

"alkyl" means the monovalent residue remaining after removal of a hydrogen atom from a saturated linear or branched chain hydrocarbon having 1 to 14 carbon atoms;

"aryl" means the monovalent residue remaining after removal of a hydrogen atom from an aromatic compound (single ring and multi- and fused-cyclic) having 5 to 12 ring atoms and includes substituted aromatics such as lower alkaryl and aralkyl, lower alkoxy, N,N-di(lower alkyl)amino, nitro, cyano, halo, and lower alkyl carboxylic ester, wherein "lower" means C-1 to C-4;

"azlactone" means 2-oxazolin-5-one groups of Formula I and 2-oxazin-6-one groups of Formula II;

"cycloalkyl" means the monovalent residue remaining after removal of a hydrogen atom from a saturated cyclic hydrocarbon having 3 to 12 carbon atoms;

"lower alkyl" means C-1 to C-4 alkyl groups;

"Michael addition" or "Michael reaction" means the catalyzed or uncatalyzed addition of a "Michael donor", illustrated by trifluoroacetate ion (III) in the equation below, to a "Michael acceptor", illustrated by protonated 2-vinyl-4,4-dimethylazlactone (VDM) (IV) in the equation below, to form a "Michael adduct" reaction product (V):

"Michael acceptor" means the electrophilic reactant in a Michael reaction;

"Michael adduct" means the product of a Michael reaction;

"Michael donor" means the nucleophilic reactant in a Michael reaction;

"oligo (2-alkenyl azlactones)" means polyaddition products of 2-alkenyl azlactones in which the products are characterized as having had addition occur at least once, i.e., a dimer possessing a number-average molecular weight of at least 278 in the case of VDM, to about fourteen times, i.e., a fifteen-mer possessing a number-average molecular weight of about 2000;

"oligo (VDM)" means any oligomer of VDM having 2 to 15 mer units; and

"predominantly" means at least 30 mole percent, preferably at least 50 mole percent, and more preferably at least 80 mole percent.

As disclosed herein for the first time, VDM and other 2-alkenyl azlactone monomers have been observed to undergo oligomerization when exposed to certain acid catalysts. Since effecting oligomerization/polymerization of a monomer by acidic catalysts is normally regarded as involving cationic intermediates, this result was unexpected.

DESCRIPTION OF THE DRAWINGS

FIG. 2 represents a comparison of the IR spectra of films of oligo(VDM) of Example 3 (2A), poly(VDM) of Example 19 (2B), and 2-ethyl-4,4-dimethylazlactone (EDM) (2C). Spectra were obtained using a Perkin Elmer 983 Ratio Recording Infrared Spectrophotometer.

FIG. 3 represents a comparison of the $^1$H-NMR spectra of deuterochloroform solutions of oligo(VDM) of Example 3 (3A) and poly(VDM) (3B). Spectra were obtained using a Varian XL-400 Spectrometer.

FIG. 4 represents a comparison of the $^{13}$C-NMR spectra of deuterochloroform solutions of oligo(VDM) of Example 3 (4A) and poly(VDM) (4B). Spectra were obtained ratio for oligo(VDM) was improved by recording transients over an eight hour period.

FIG. 5 represents a comparison of the ultraviolet (UV) spectra of acetonitrile solutions of oligo(VDM) of Example 22 (5A), poly(VDM) (5B), and EDM (5C) UV spectra were obtained using a Perkin-Elmer Model 330 Spectrophotometer. The absorptivity for oligo(VDM) at 331 nm was 2.52 l/g-cm.

FIG. 6 represents a comparison of the size exclusion gel permeation chromatograms of oligo(VDM) prepared by conditions outlined in Examples 21 (6A), 22 (6B), 23 (6C), and 24 (6D). GPC's were obtained in tetrahydrofuran solution using a Hewlett-Packard 1090-LUSI instrument. The column set utilized was specifically designed for the separation of materials of molecular weight of less than 10,000. Columns utilized were three 500 Å columns (1×50 cm+2×25 cm) from Jordi Associates (Millis, Mass.). Molecular weight data were based on calibration using polystyrene standards available from Pressure Chemical Co. (Pittsburgh, Pa.).

DETAILED DESCRIPTION OF THE INVENTION

The present invention provides novel azlactone-functional oligomers possessing structures selected from the group consisting of:

A) oligomers possessing structures depicted by general Formula VI wherein $R^1$ and $R^2$ independently represent an alkyl group of 1 to 14 carbon atoms, a cycloalkyl group of 3 to 12 carbon atoms, an aryl group of 5 to 12 ring atoms, or $R^1$ and $R^2$ taken together with the carbon atom to which they are joined form a carbocyclic ring of 4 to 12 ring atoms;

$R^3$ and $R^4$ are independently hydrogen or lower alkyl;

n is 0 or 1;

Az is a symbol for an azlactone group bonded in the 2-position in which $R^1$, $R^2$, $R^3$, $R^4$, and n are as defined above:

G independently can be hydrogen, methyl, and groups selected from —$CH_2CHGAz$, —$CH_2C$-$G(Az)CH_2CHGAz$, —$CH_2CG(Az)[CH_2C$-$G(Az)]_pCH_2CGAz$, and p can have integral values from 0 to about 12, with the proviso that the extent of oligomerization does not exceed a total number-average molecular weight of about 2000 for the oligomers depicted by Formula VI;

r can be 0 or 1; and q can have integral values from 1 to about 12.

B) oligomers possessing structures depicted by general Formulae VIIA and VIIB wherein

X is the covalently bonded counter ion or gegenion of a Bronsted acid whose pKa is less than 1.2, or X can be a 3-quaternized 2-alkenyl azlactone group of Formula VIII in which $R^5$ can be hydrogen or methyl and all other symbols are as previously defined; and Az and G are as defined above, except that at most one G can be hydrogen or methyl in Formula VIIA when X is not a 3-quaternized 2-alkenyl azlactone group, and in Formula VIIB G cannot be H or $CH_3$.

C) oligomers possessing structures depicted by general Formula IX wherein Az, G and q are as previously defined.

The oligomers of the invention are prepared by the acid catalyzed oligomerization of 2-alkenyl azlactones of Formula X.

wherein $R^1$, $R^2$, $R^3$, $R^4$, $R^5$, and n are as defined above.

Useful 2-alkenyl azlactones include:

2-vinyl-4,4-dimethyl-2-oxazolin-5-one [also called 2-vinyl-4,4-dimethylazlactone or VDM],
2-isopropenyl-4,4-dimethyl-2-oxazolin-5-one,
2-vinyl-4-ethyl-4-methyl-2-oxazolin-5-one,
2-vinyl-4,4-dimethyl-1,3-oxazin-6-one, and others whose preparations are disclosed in U.S. Pat. No. 4,304,705 which is incorporated herein by reference. A preferred 2-alkenyl azlactone is VDM (available from SNPE, Inc., Princeton, N.J.).

Both Bronsted and Lewis acidic materials are effective catalysts for the oligomerization. Bronsted acids are classical proton donating materials, and useful catalysts are relatively highly acidic possessing pKa's of less than about 1.2. Useful Bronsted acid catalysts include sulfuric acid, hydrogen chloride, hydrogen bromide, hydrogen iodide, trifluoroacetic acid, trichloroacetic acid, trifluoromethanesulfonic acid, p-toluenesulfonic acid, perchloric acid, and ethanesulfonic acid. Useful Lewis acids (which broadly encompass Bronsted acids in their role as electron pair acceptors) include aluminum chloride, zinc chloride, boron trifluoride, antimony pentachloride, titanium tetrachloride, and iodine. In general the rate of oligomerization is directly related to acid strength of the catalyst. A further consideration for the choice of a proper catalyst, however, is the influence that very strong acids, e.g., pKa's $< -3$, have on the stability of the azlactone oligomeric product. Employment of these very strong acids requires that the azlactone oligomeric product be handled in a water-free environment, as the product will quickly hydrolyze with adventitious moisture in the presence of these very strong acids. Although longer oligomerization times are required with more weakly acidic catalysts, the resultant oligomeric azlactone product is less sensitive to hydrolysis. Preferred catalysts are trifluoroacetic acid and boron trifluoride for 2-vinyl ($R^5$=H) substituted azlactones; ethanesulfonic acid is preferred for 2-isopropenyl ($R^5$=$CH_3$) substituted azlactones. Useful amounts of the catalysts are from 0.1 to 50 mole percent (based on 2-alkenyl azlactone), preferably 1.0 to 25 mole percent, and more preferably from 1.0 to 10 mole percent.

Although the oligomerization reaction can be conducted without solvent, for purposes of control and uniformity of product a solvent is generally employed. Aside from the desirability of an effective solvent to dissolve both reactants and oligomeric products, the solvent contains no hydroxyl, thiol, or amine groups capable of undergoing a ring-opening reaction with the azlactone heterocycle. Useful organic solvents include chloroform, dichloromethane, 1,2-dichloroethane, toluene, diethyl ether, acetone, methyl ethyl ketone, ethyl acetate, acetonitrile, especially acetic acid, and mixtures thereof. The nature of the solvent is not without affect on the oligomerization process, and generally higher rates of oligomerization are observed with increasing solvent dielectric constant. A possible rationale for this observation is that the oligomerizing species are ionically charged, and ions simply are more stable in higher dielectric media. Acetic acid was specifically noted as being an effective solvent because of its high dielectric constant and because it may actually participate in the oligomerization reaction by creating enolizable hydrogens through initial Michael addition, vide infra. Useful concentrations of these solvents are generally from 0.9 to 0.1, preferably 0.7 to 0.2, and more preferably 0.5 to 0.3 weight fraction of the reaction solution.

The oligomerization reaction rate can also be enhanced by increasing the temperature. Preferred reaction temperatures range from 20° to 100° C.

Corresponding reaction times vary depending on the previously mentioned factors such as catalyst, catalyst concentration, solvent, solvent concentration, and reaction temperature. Generally reaction times range from a few hours to several days. Progress of reaction is conveniently monitored by gas chromatography observing the disappearance of 2-alkenyl azlactone relative to the solvent.

Figure 1:
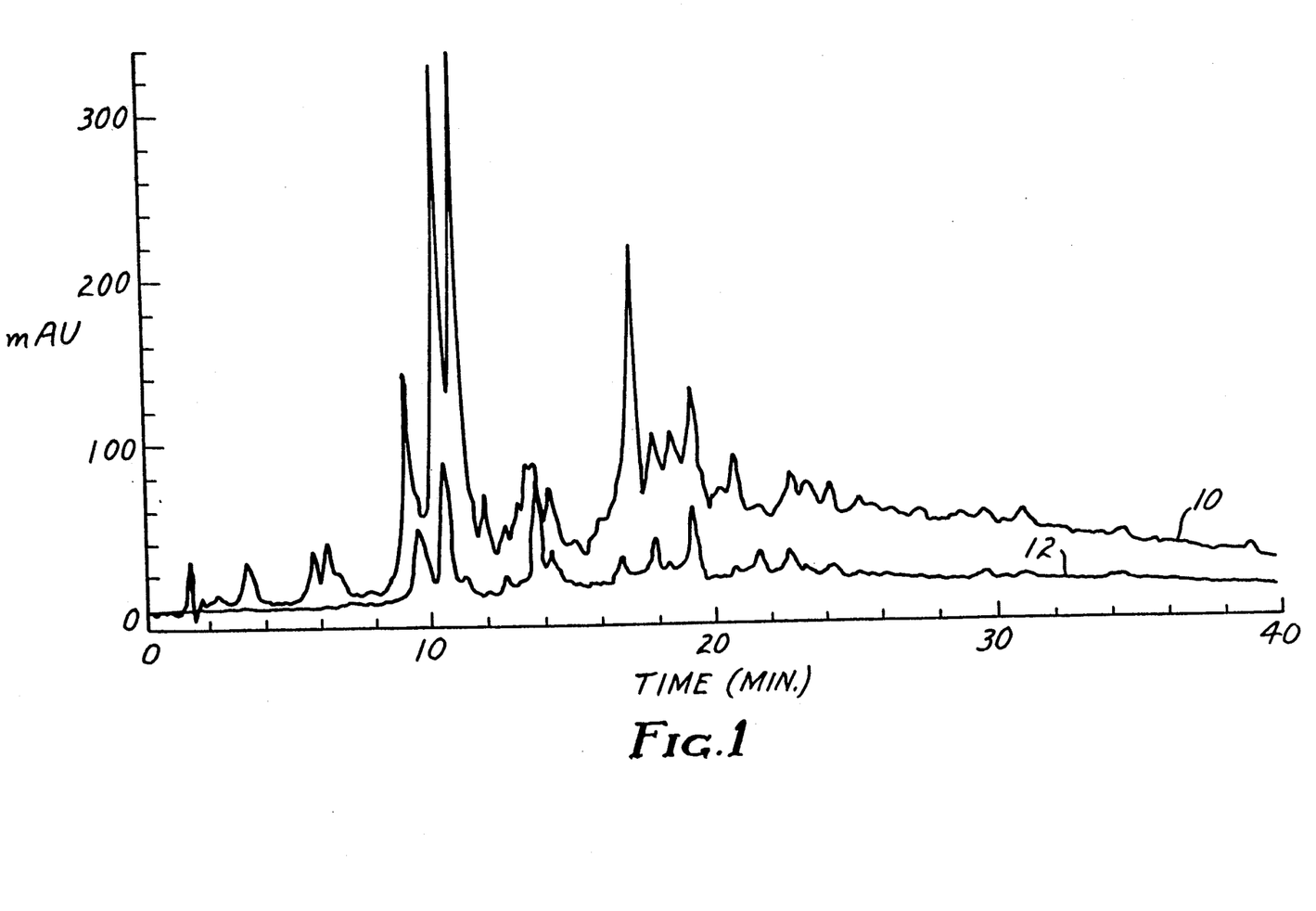
FIG. 1 is a high pressure liquid chromatogram measuring ultraviolet light absorption versus time for the partially hydrolyzed oligo(VDM) sample of Example 1.

The complexity of the oligomerization reaction is evident from the hplc chromatogram of FIG. 1 in which the presence of more than 30 products can be detected. Some of these are also highly colored as indicated by the lower trace in FIG. 1 suggesting significantly different kinds of structures in which electrons can be highly delocalized. While not wishing to be bound by any explanation or reaction mechanism and yet to disclose the invention in as precise terms as possible, the following characteristics are supported by the experimental examples.

1) That oligomerizing monomer is the protonated 2-alkenyl azlactone is supported by the fact that only strong acids capable of protonating (or engaging in acid-base complexation in the case of Lewis acids and to facilitate discussion only protons will be considered in subsequent explanations) the nitrogen of the azlactone function are effective catalysts. Also, increasing the concentration of acid (and protonated azlactone) dramatically increases the rate of oligomerization.

2) The overall oligomerization begins by Michael addition to the protonated 2-alkenyl azlactone to generate reactive ketenaminal structures. In an inert solvent the protonated monomer generally has two nucleophilic agents with which it can react, the counter ion or gegenion (X$^-$) of the acid catalyst and the 2-alkenyl azlactone (represented by VDM below:)

wherein in all charts
Me=methyl
X and VDM are as previously defined.

An important aspect of the above reactions is that initial Michael addition to form the reactive ketenaminals is favored strongly because the Michael adducts can undergo stabilization because of the tautomeric equilibrium possible when a proton can shift from azlactone nitrogen to alpha-carbon of the original 2-alkenyl group. That this stabilization is very important was strongly supported by the inability of a methylating agent (methyl p-toluenesulfonate) to initiate oligomerization; analogous shifts of methyl groups do not generally take place.

That hydrogens on carbons adjacent to azlactone groups can enolize to reactive ketenaminal forms and participate in the oligomerization was clearly supported by incorporation into the oligomeric framework of azlactones possessing saturated alkyl groups at position-2 (see Example 27).

Whether the gegenion or VDM adds to the protonated VDM is largely determined by the nature and nucleophilicity of the gegenion. With carboxylate ions, for example, the gegenion reaction can be very important, whereas with stronger acid gegenions such as perchlorate, sulfate, and triflate the gegenion reaction may be less important.

3) The ketenaminals engage in oligomerization with protonated VDM in the following manner:

Case 1: Gegenion Michael addition

Proton loss from the penultimate group is an important issue. VDM is the strongest base or proton acceptor in the system because its positively charged conjugate acid can be stabilized by charge delocalization (not possible with other azlactones possessing saturated alkyl groups in the 2-position) in the following manner:

Continued oligomerization can continue from both the remaining methine hydrogen of the original Michael adduct or from the two new methylene hydrogens in the newly added VDM.

Case 2: VDM Michael addition

-continued

↓ higher heterocyclo-
containing (backbone)
oligomers
VI

The initial Michael adduct can oligomerize in the manner of gegenions just described in Case 1 or it can cyclize to form six- or eight-membered ring compounds which result from either C- (six-membered) or N-(eight-membered) Michael addition of the ketenaminal to the positively charged Michael adduct of the initial Michael addition. Once this cyclization has occurred, additional oligomerization can take place from the ketenaminal portion and/or the enolizable methine (in the six-membered ring) portion of the ring structures.

An additional feature of Case 2 type oligomerizations is that the initial positively charged, alkylated VDM portion of the adduct may not persist over the course of oligomerization. Cyclization (either C- or N-) and loss of a proton can take place even at later stages of oligomerization to generate larger heterocycles as well, such as Formula VI when q is at least 2 or with Formula IX compounds.

An important distinction between the oligomers of the present invention compared to the analogous systems mentioned in the background section is that the present oligomers are oligomerized predominantly through the 2-alkenyl groups, i.e., they consist of "vinyl units" as depicted earlier. In contrast, the oxazoline systems were either exclusively or predominantly (80%) polymerized or oligomerized via "Michael units" created by N-Michael addition of the oxazoline ring nitrogen to the 2-alkenyl group. Examination of the $^1$H-NMR spectrum for oligo(VDM) in FIG. 3A and integration of the resonances greater than 3 ppm reveals that at most 10% of the oligomeric products are comprised of Michael units.

Objects and advantages of this invention are further illustrated by the following examples, but the particular materials and amounts thereof recited in these examples, as well as other conditions and details, should not be construed to unduly limit the invention. Examples 1 through 18 deal in general with important variations in the process of synthesizing oligo(2-alkenyl azlactones), Examples 19 through 28 deal with characterization, and Example 29 examines one utilization of the oligomeric products of the invention.

EXAMPLE 1

This example teaches use of a Bronsted acid catalyst to effect the oligomerization of VDM.

VDM (350 grams; 2.517 moles), methyl ethyl ketone (MEK, 350 grams), 2,6-di-t-butyl-4-methylphenol (BHT, available from Aldrich Chemical Co., Milwaukee, Wis., employed as a stabilizer to prevent any free radical polymerization) (0.70 gram), and trifluoroacetic acid (TFA, available from Aldrich Chemical Co.) (1435 grams; 0.126 mole) were placed in a sealed glass bottle. The bottle was placed in an Atlas Launderometer (available from Atlas Electric Devices Co., Chicago, IL) at 60° C. for 22.5 hours. During the reaction time the initially colorless solution of reactants turned red in color. Progress of the oligomerization was measured by gas chromatography observing the disappearance of VDM relative to the MEK solvent. Percent conversion to higher molecular weight products was 97.8%. Removal of the solvent in vacuo left an orange friable foamy product. The product was shown to be a multicomponent mixture by hplc analysis, and a chromatogram is shown in FIG. 1. The solid azlactone-functional product was exposed to 70% relative humidity at 22° C. for 36 h during which the azlactone C=O at about 5.5 micrometers disappeared due to ring-opening hydrolysis. A sample was injected onto a 15 cm×4 mm (id) Hamilton PRP [poly(styrene-co-divinylbenzene), available from the Hamilton Co., Reno, Nev.] column and eluted with water acetonitrile mixtures also containing 0.1% by volume trifluoroacetic acid. In the period from 0 to 45 minutes, the eluting solvent varied from wateracetonitile 90:10 to 60:40 mixtures; from 45 to 60 minutes the mixtures varied from 60:40 to 20:80. Upper trace 10 represents components absorbing 210 nm incident ultraviolet light, while lower trace 12 represents those components absorbing 325 nm light and which manifest visible color.

EXAMPLES 2-6

These examples teach that useful Bronsted acids possess pKa's of less than 1.2.

The reactions to assess the activity of the various catalysts in oligomerizing VDM were conducted at 22° C. in ethyl acetate solvent (solvent weight fraction 0.6) and using 5 mole percent of the catalyst. Percent conversions were determined using the gas chromatography procedure of Example 1. The results are given in the following table:

| Example | Bronsted Acid Catalyst | pKa | % Conversion After 18 h |
|---|---|---|---|
| 2 | Perchloric Acid | −8 | 72 |
| 3 | Trifluoroacetic Acid | 0.23 | 40 |
| 4 | Trichloroacetic Acid | 0.66 | 40 |
| 5 | Dichloroacetic Acid | 1.25 | 3 |
| 6 | Acetic Acid | 4.76 | <1 |

EXAMPLES 7-9

These examples teach that Lewis acidic materials can also be effective catalysts for promoting oligomerization.

Reactions were conducted at 22° C in acetonitrile (solvent weight fraction =0.5) and using 5 mole percent catalyst. Percent conversions were again determined using gas chromatography, and the results are given in the following table:

| Example | Lewis Acid Catalyst | % Conversion After 72 h |
|---|---|---|
| 7 | Aluminum Chloride | 25 |
| 8 | Boron Trifluoride Etherate | 78 |
| 9 | Zinc Chloride | 21 |

EXAMPLE 10

This example teaches increased oligomerization rates can be achieved by increasing reaction temperature.

Employing the procedure of Example 3, i.e., 40 wt. % VDM in ethyl acetate, 5 mole percent TFA, and a 24 h reaction time, percent conversions were measured at three reaction temperatures. At −2° C. 22%, at 22° C. 43%, and at 59° C. 88% VDM had undergone oligomerization.

EXAMPLE 11

This example teaches that increasing catalyst concentration increases oligomerization rate.

Employing the procedure of Example 3 except that 0, 1.0, 5.0, and 7.2 mole percent TFA concentration levels were employed, after 20 h the percent conversions were 0, 10, 42, and 59%, respectively.

EXAMPLES 12-16

These examples teach that increased oligomerization rates may be achieved by employing solvents of increased dielectric constants ($\epsilon$).

The examples shown in the table below were conducted using 0.5M concentrations of VDM in the various solvent mixtures, 5 mole percent TFA, and 7 days at 22° C.

| Example | MEK:Chloroform Volume Ratio | $\epsilon$ | % Conversion |
|---|---|---|---|
| 12 | 100:0 | 18.5 | 57 |
| 13 | 75:25 | 15.1 | 56 |
| 14 | 50:50 | 11.6 | 51 |
| 15 | 25:75 | 8.2 | 45 |
| 16 | 0:100 | 4.7 | 36 |

EXAMPLE 17

This example teaches that 2-isopropenyl azlactones undergo oligomerization as well but generally require stronger acidic catalysts than their 2-vinyl azlactone counterparts.

2-Isopropenyl-4,4-dimethylazlactone (IDM) was synthesized by the method of Taylor et al., *J. Polym. Sci. Polym. Lett.*, 9, 187 (1971). The procedure of Example 3 was employed except that IDM was utilized instead of VDM and ethanesulfonic acid (pKa=0) instead of TFA. After 4 days at 22° C., 20.1% of the IDM had been oligomerized into higher molecular weight products; TFA was not as effective under the same conditions.

EXAMPLE 18

This example teaches that six-membered ring 2-alkenyl azlactone compounds undergo oligomerization as well 2-Vinyl-4,4-dimethyl-2-oxazin-6-one (VOX) was prepared by the method of Heilmann et al., *J. Polym. Sci.: Polym. Chem. Ed.*, 1984, 22, 1179.

The oligomerization was conducted by VOX in ethyl acetate (solvent weight fraction =0.6) and using TFA (5 mol %) as catalyst. The solution was heated at 70° C. for 19 h. The conversion to oligomeric products was 25%.

EXAMPLE 19

This example teaches that the azlactone functional group remains intact after oligomerization.

Figure 2A:
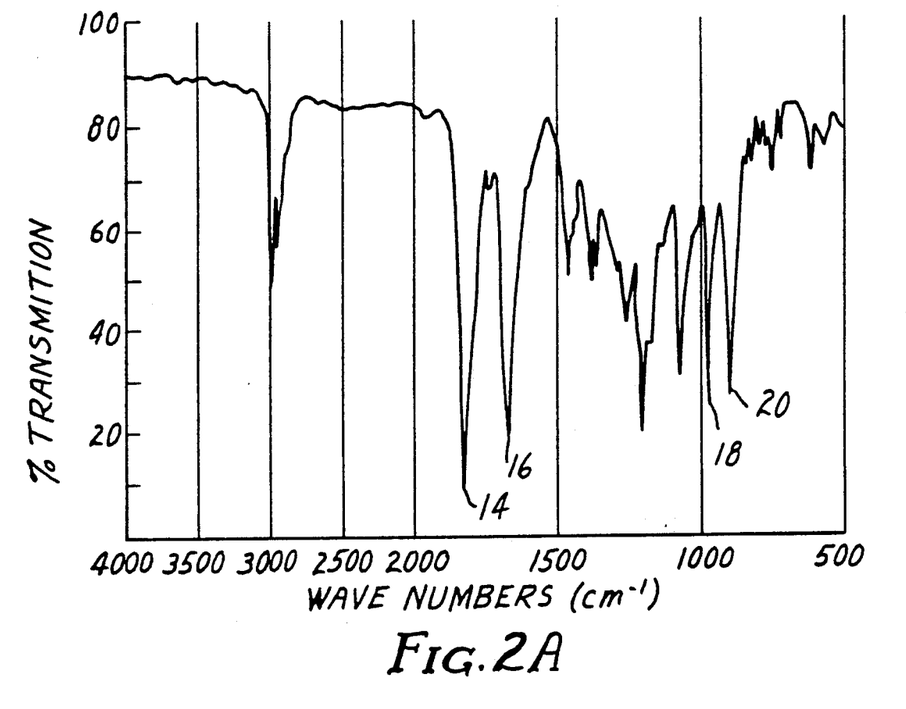
Figure 2B:
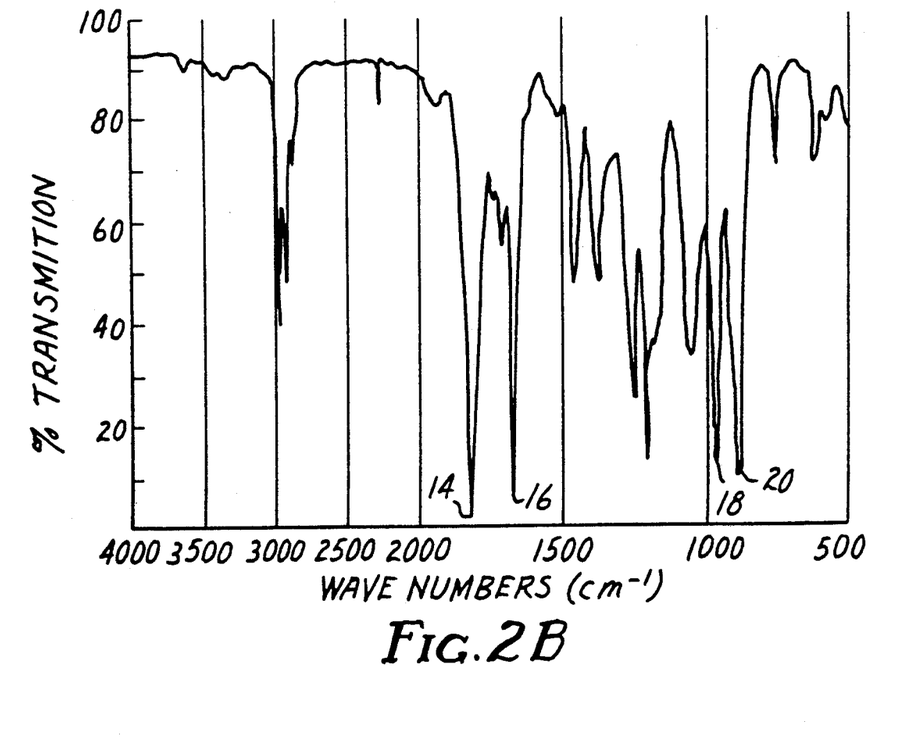
Figure 2C:
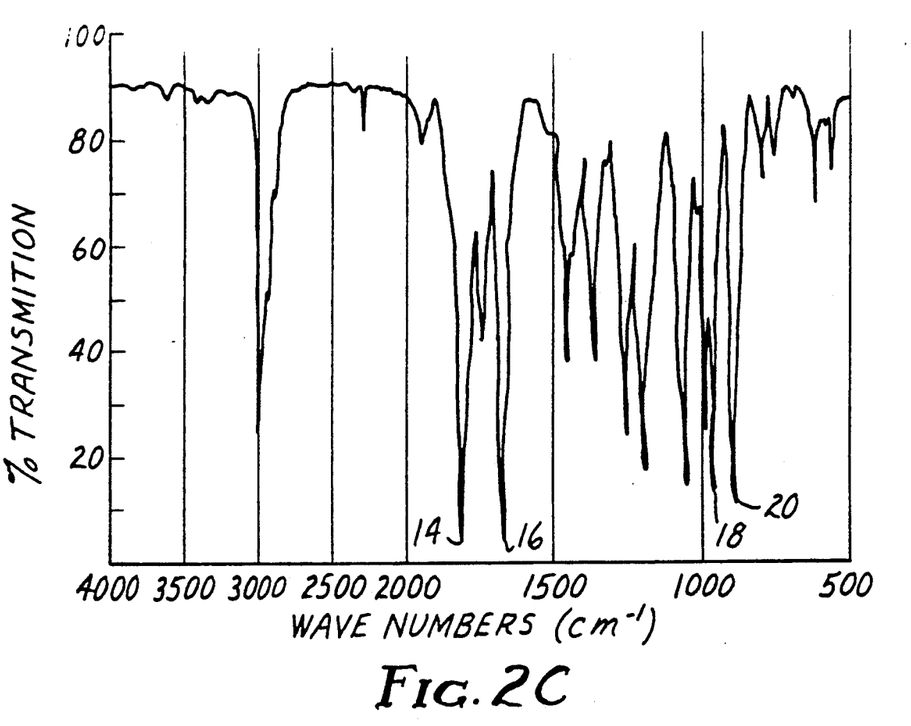

In FIG. 2 are presented three infrared spectra. Spectrum 2A is of a film of oligo(VDM) prepared by the method of Example 3. Spectrum 2B is of a film of poly(VDM) prepared in methyl ethyl ketone (MEK) at 31.3% solids using azobis(isobutyronitrile) (AIBN) (0.5 wt. %) as initiator at 60° C for 18 h; the weight-average molecular weight as determined by size exclusion chromatography was 135,000. Spectrum 2C is of 2-ethyl-4,4-dimethylazlactone (EDM) prepared by the method of Rasmussen et al., *J. Polym. Sci.: Polym. Chem. Ed.*, 1986, 24, 2739.

The oligo(VDM) is thus compared directly to two azlactones, one a mixture of high molecular weight polymers and the other a pure low molecular weight compound, that contain saturated alkyl groups at position-2. The comparison of the carbonyl absorption peaks 14 in FIGS. 2A, 2B, and 2C at about 1820 cm$^{-1}$, the carbon-nitrogen double bond stretching absorption peaks 16 at about 1675 cm$^{-1}$, and two absorption peaks 18 and 20 attributed to the azlactone heterocycle in the fingerprint region at about 965 and 895 cm$^{-1}$ shows that less than a 5 cm$^{-1}$ variation exists among all three spectra at these intense absorption regions.

EXAMPLE 20

This example elaborates some of the differences in various spectra of poly(VDM) and oligo(VDM).

Figure 3A:
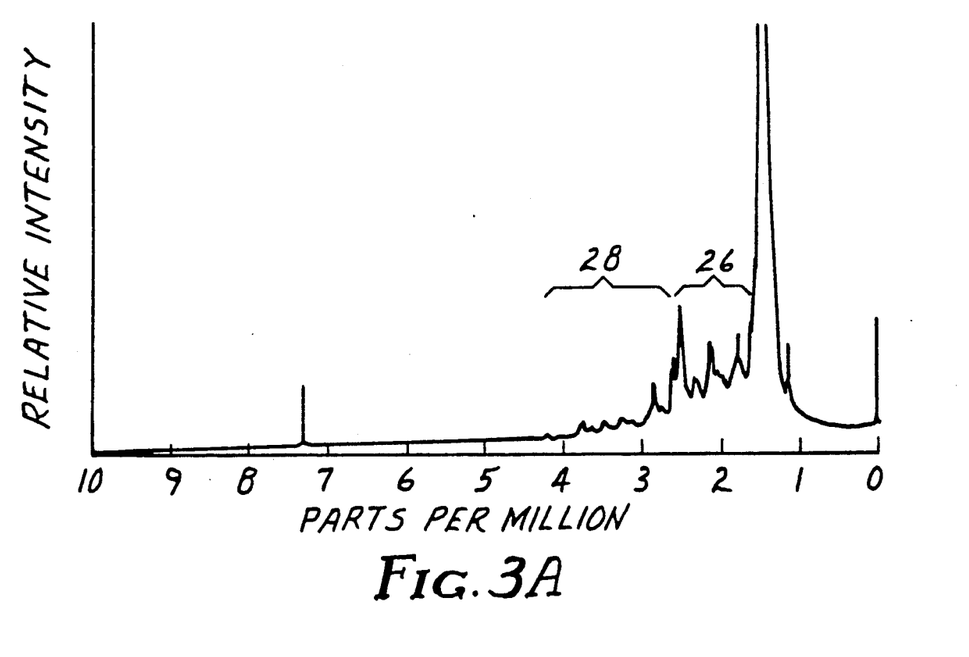
Figure 3B:
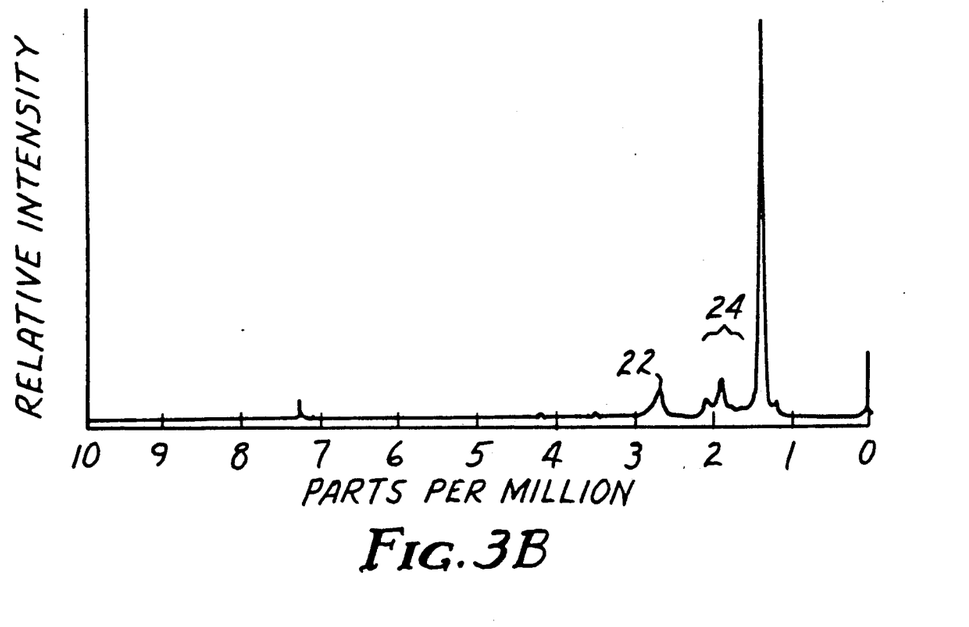

FIG. 3 shows the $^1$H-NMR spectra of poly(VDM) (3B) and oligo(VDM) (3A). Noteworthy features in the spectrum of poly(VDM) are broadened resonances indicative of high molecular weight and the relative positions of backbone methine resonance 22 at 2.7 ppm and methylene resonances 24 at 1.6-2.2 ppm as shown in FIG. 3B. Resonances for oligo(VDM) are not nearly as broad, and fine structure, i.e., multiplets derived from coupling, is still evident which indicates lower molecular weight. In addition to many resonances in the expected range of resonances 26 from 1.6-2.7 ppm for methylene and methine, additional resonances 28 are observed downfield to about 4 ppm which may be attributed to methylenes/methines adjacent to heteroatoms or that are contained in relatively strained cyclic structures.

Figure 4A:
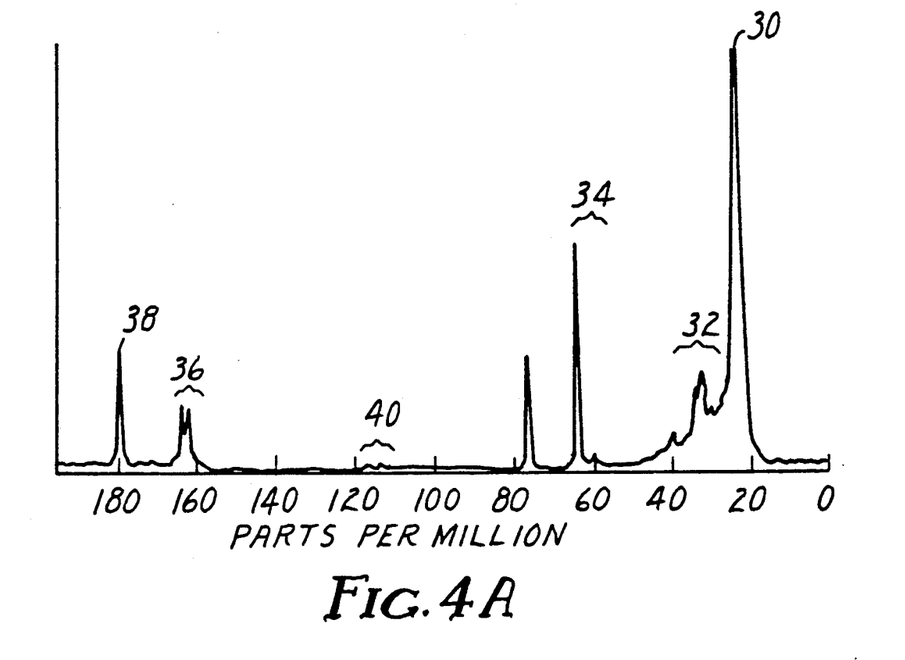
Figure 4B:
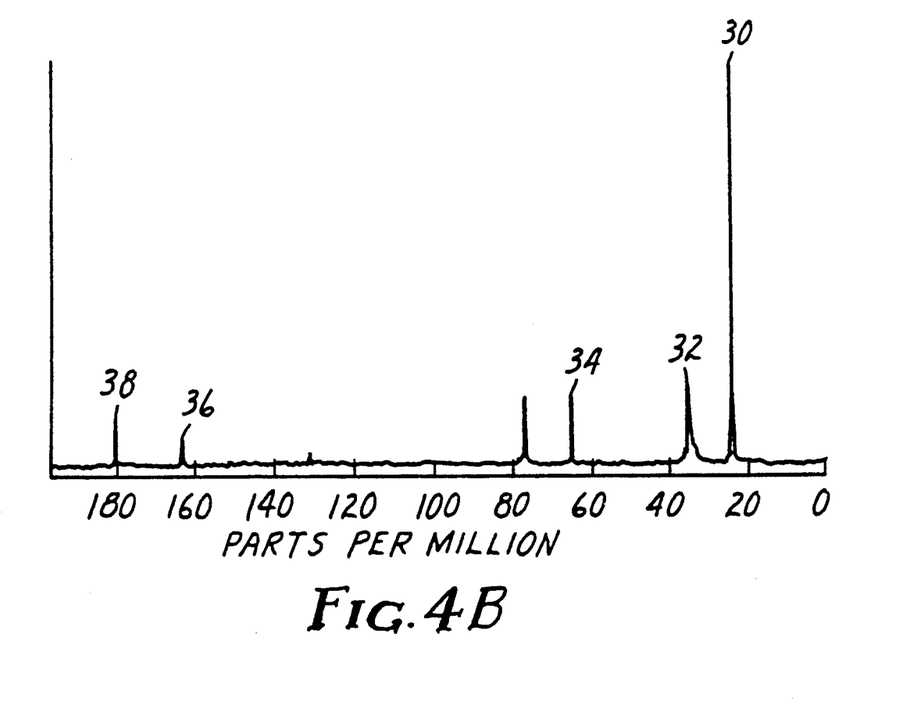

FIG. 4 shows the $^{13}$C-NMR spectra of poly(VDM) (4B) and oligo(VDM) (4A). The poly(VDM) spectrum is relatively straight forward with a gem-dimethyl carbon resonance 30 at 24 ppm, methylene and methine carbon resonances 32 between 32-36 ppm, the quaternary carbon resonance 34 at 65 ppm, the C=N resonance 36 at 163 ppm, and the C=O resonance 38 at 180 ppm. Oligo(VDM) is similar but with significant differences being observed in the methylene/methine and C=N regions. Also, resonances 40 at 116 and 113 may be indicative of minor amounts of olefinic carbons.

Figure 5A:
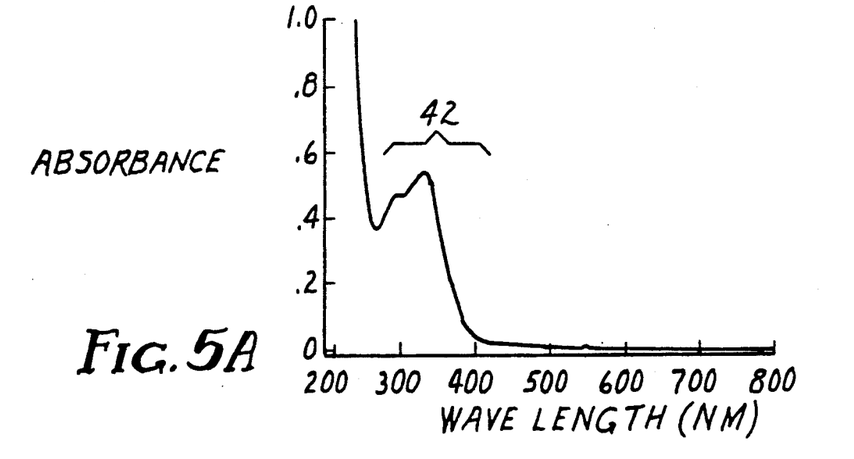
Figure 5B:
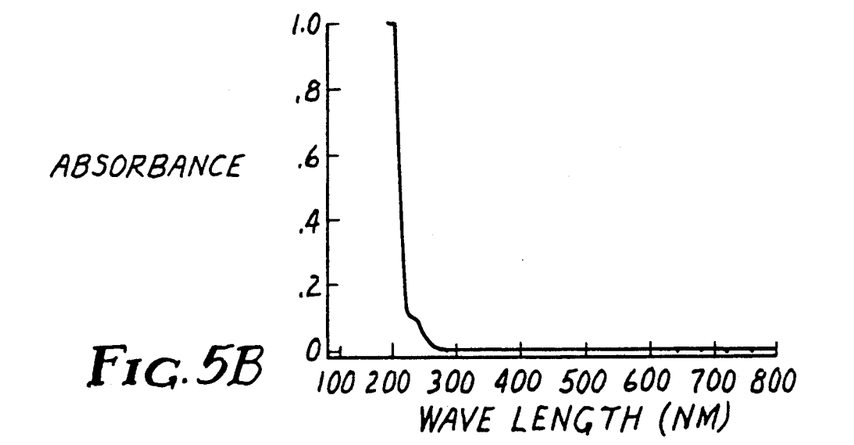
Figure 5C:
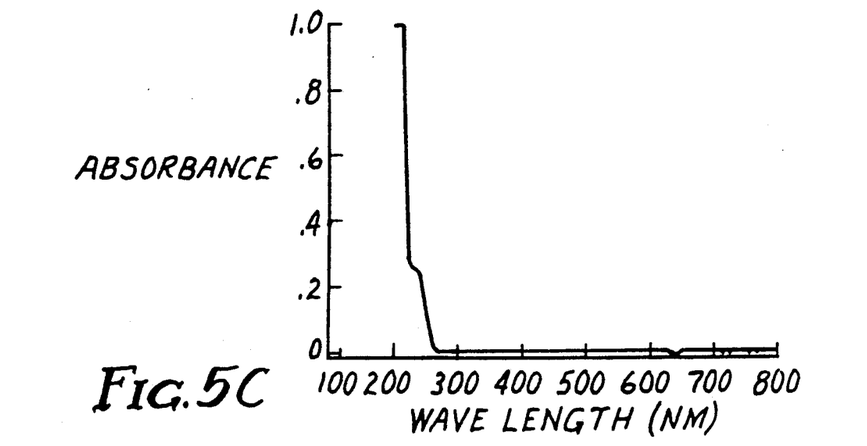

The UV spectra of FIG. 5, perhaps more than the other spectroscopic methods, point out significant differences between oligo(VDM) (5A) and the conventional azlactones poly(VDM) (5B) and EDM (5C). The latter two azlactones exhibit essentially no absorption above 300 nm, while the oligo(VDM) material must contain at least a small number of chromophores involving extended, conjugated systems to account for the significant absorption 42 above 300 nm ($\lambda_{max}=331$).

EXAMPLE 21

This example teaches that the product of the acid-catalyzed reaction is comprised of relatively low molecular weight components.

In the absence of termination reactions and in systems in which the initiating species operates with unit efficiency, degree of polymerization or oligomerization (and ultimately number-average molecular weight) can be calculated for addition polymers using the following relationship:

$$X_N = \frac{[M]}{[I]}$$

where
$\overline{X}_N$ = degree of polymerization or oligomerization
[M] = molar concentration of monomer
[I] = molar concentration of initiator It therefore follows that molecular weight in such systems should be quite sensitive to initiator concentration.

When the oligomerization of VDM was conducted in ethyl acetate (solvent weight fraction 0.6) with varying amounts of TFA initiator, however, molecular weight was shown to be quite insensitive to initiator concentration. The data in the following table indicate that the molecular weight is very low compared to predicted values and remains quite constant regardless of initiator concentration.

| TFA, mol % | Calculated $\overline{M}_N$ | Determined $\overline{M}_N{}^A$ | | |
|---|---|---|---|---|
| | | GPC$^B$ | Rast Camphor$^C$ | VPO$^D$ |
| 1.0 | 13,900 | 701 | — | — |
| 2.0 | 6,950 | 770 | — | 582 |
| 4.0 | 3,475 | 806 | 794 | — |
| 8.0 | 1,737 | 788 | — | 572 |

$^A$ = All oligo(VDM) samples were further reacted with excess n-butylamine in order to generate non-reactive materials for characterization. The resulting ring-opened materials were twice precipitated into diethyl ether and dried under vacuum.
$^B$ = Gel permeation chromatography (GPC) was conducted in tetrahydrofuran (THF) solution employing a series of Toyo Soda Manufacturing Co. columns (G3000, G2000, and G1000 available from Phenomenex, Rancho Palos Verde, CA), one microstyragel column (500 Å available from Waters Chromatorgraphy Division, Millipore Corp., Milford, MA), and one Waters microstyragel column (100 Å) repacked by Analytical Sciences, Inc. (Santa Clara, CA). Molecular weights were determined by comparison to polystyrene standards.
$^C$ = The procedure utilized was that outlined in A.I. Vogel, "A Textbook of Practical Organic Chemistry," 3rd Edition, Longman Group Limited: London, 1970, p. 1037.
$^D$ = Vapor Phase Osmometry (VPO) was conducted in THF solution by Arro Laboratory, Inc. (Joliet, IL).

EXAMPLES 22-25

These examples demonstrate the variablity in distribution of oligomers depending on such factors as the nature of initiating acid and solvent.

The examples in the table below were all conducted at 22° C. using 5 mole percent of the initiating acid and a solvent weight fraction of 0.5.

Figure 6A:
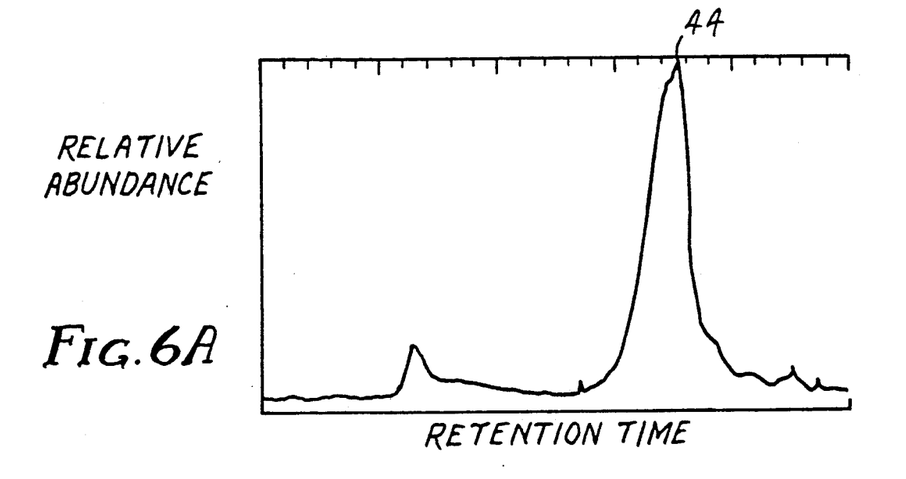
Figure 6B:
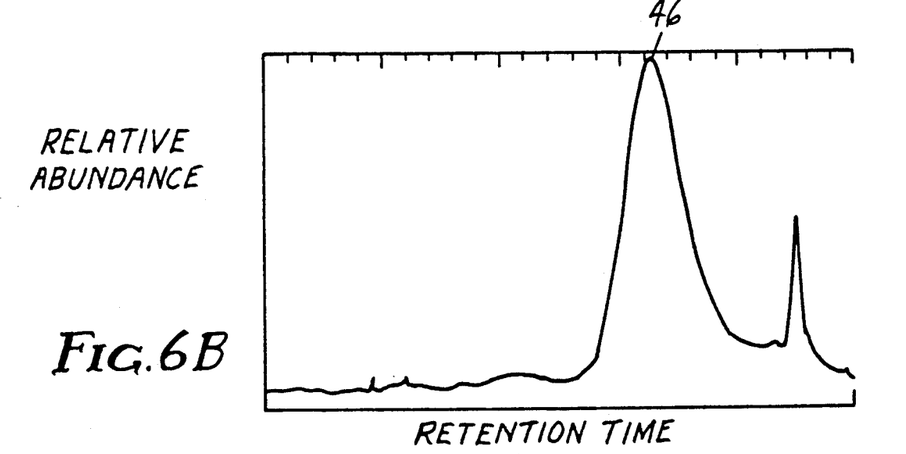
Figure 6C:
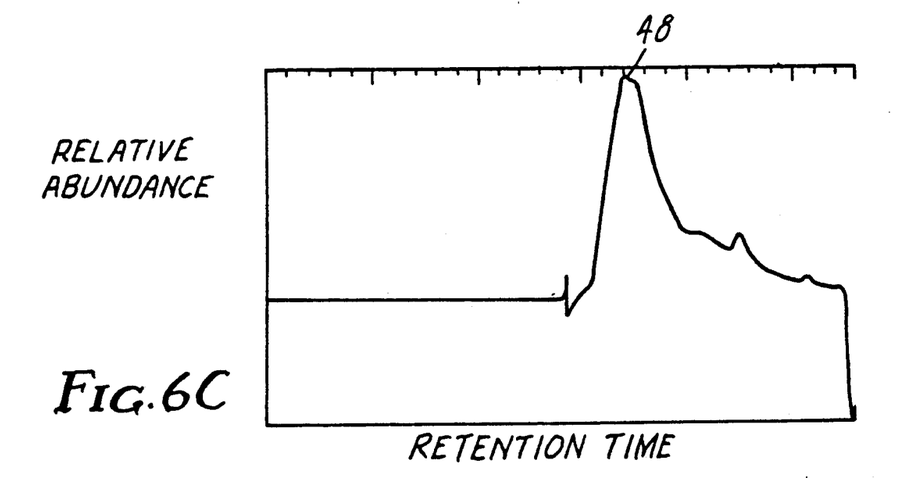
Figure 6D:
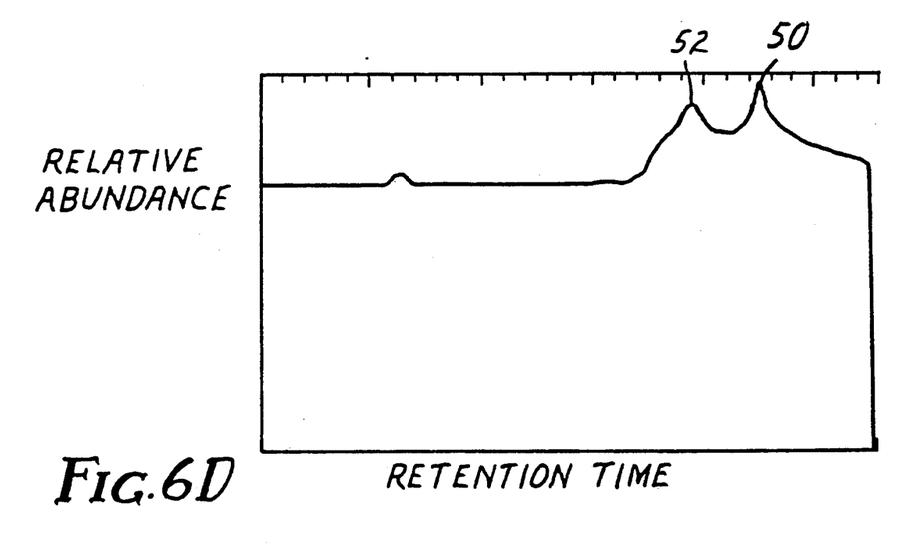

| Example | Catalyst | Solvent | GPC | Peak MW (No.) |
|---|---|---|---|---|
| 22 | TFA | aceto-nitrile | FIG. 6A | 718 (44) |
| 23 | TFA | acetic acid | FIG. 6B | 1001 (46) |
| 24 | ethanesulfonic acid | aceto-nitrile | FIG. 6C | 853 (48) |
| 25 | sulfuric acid | aceto-nitrile | FIG. 6D | 257 (50) 502 (52) |

These size exclusion chromatograms reveal that the majority of products has molecular weights of less than 2000, although a small amount of intermediate molecular weight products, ca. 20,000, is produced in some instances.

EXAMPLE 26

This example provides specific evidence for oligomers possessing degrees of oligomerization of up to The oligomer of Example 25 was poured into a crystallizing dish and allowed to air dry (at 70% relative humidity) for 24 hours. IR analysis indicated that the azlactone carbonyl absorption had disappeared. The partially hydrolyzed oligomer was dissolved in dithiothreitol and examined by Fast Atom Bombardment (FAB) Mass Spectrometry. Among other peaks in the spectrum were the following with possible assignments:

| m/e | Possible Assignment* |
|---|---|
| 611 | 4(VDM) + 3 waters + 1 |
| 768 | 5(VDM) + 4 waters + 1 |
| 925 | 6(VDM) + 5 waters + 1 |
| 1082 | 7(VDM) + 6 waters + 1 |
| 1239 | 8(VDM) + 7 waters + 1 |
| 1396 | 9(VDM) + 8 waters + 1 |

* = where, for example, 4 (VDM) + 3 waters + 1 indicates a chemically protonated tetramer wherein 3 of the azlactone rings have been ring-opened with water, i.e. hydrolyzed;
m/e = mass/charge

EXAMPLE 27

This example teaches that hydrogens on carbons adjacent to azlactone rings are labile and can be substituted by 2-alkenyl azlactone residues.

A solution containing deuterochloroform (3.94 grams), EDM (1.41 grams; 0.01 mole), and TFA (1.25 grams; 0.011 mole) was prepared and cooled to −78° C.

Me = methyl

VDM (1.39 grams; 0.01 mole) was added in a stream without incident. Upon warming to room temperature, the solution became yellow and slightly viscous. After 3 days at 22° C., the $^1$H-NMR contained in addition to a normal oligo(VDM) spectrum a doublet centered at 1.34 ppm (relative to tetramethylsilane) indicative of the —CHCH$_3$—group of the incorporated EDM; integration revealed that 31% of the EDM charged was incorporated. GC-MS analysis employing electron impact revealed the presence of an EDM:VDM dimer (m/e=280). This result indicated that methylene hydrogens adjacent to an azlactone group are able to participate in the oligomerization reaction.

Similarly, 2-isopropyl-4,4-dimethylazlactone prepared by the method of Rasmussen et al., *J. Polym. Sci.: Polym. Chem. Ed.*, 1986, 24, 2739 (b.p.=91°-92° C. at 60 Torr.) was subjected to the same reaction conditions as the EDM above. A gem-dimethyl resonance for the incorporated 2-isopropyl material was observed in the $^1$H-NMR as a singlet at 1.34 ppm. GC-MS analysis showed a molecular ion for the 1:1 adduct with VDM at m/e=294. The data of this Example show that methine hydrogens adjacent to azlactone groups may also participate in the oligomerization reaction.

EXAMPLE 28

This example teaches that oligomerization occurs only with immonium ion generating agents that can be readily 1,3-shifted, such as a proton or other Lewis acid.

In this trial a methyl group was utilized as a non-removable immonium ion generating agent. The oligomerization of VDM was examined in acetonitrile solution (solvent weight fraction 0.6) at 22° C. by adding 7.2, 16.4, and 49.2 mol % (based on VDM) of methyl p-toluenesulfonate. After 96 h, the reactions were examined by gas chromatography, and the corresponding amounts of VDM that were unaccounted for were 7.8, 16.5, and 44.1 mole %, respectively. Thus, although the methylating agent did apparently form the immonium ion by reaction with VDM accounting for the 1:1 correspondence in methylating agent charged to undetected VDM, VDM does not react, i.e., undergo oligomerization, with the VDM-Me$^+$immonium ion. A possible reationale is that Michael addition of VDM to VDM-Me$^+$creates an unstable ketenaminal that cannot undergo stabilization by a 1,3-shift as is possible with the acid catalysts of the invention.

EXAMPLE 29

This example teaches utilization of oligo(VDM) as a crosslinker for a pressure sensitive adhesive.

Preparation of Copoly[Iso-octyl Acrylate: N-Vinylpyrrolidinone:Hydroxyethyl Methacrylate (88:8:4 w/w/w)]

The following ingredients were charged into a glass bottle:

| | |
|---|---|
| Iso-octyl Acrylate (IOA) | 66.0 grams |
| N-Vinylpyrrolidinone (NVP) | 6.0 grams |
| Hydroxyethyl Methacrylate (HEMA) | 3.0 grams |
| MEK | 75.0 grams |
| AIBN | 0.15 gram |

The resulting solution was deoxygenated using a nitrogen sparge, sealed, and heated at 55° C. for 24 h in a launderometer. Conversion to copolymer was 98.8% as measured gravimetrically after volatilization of solvent and unreacted monomers.

Evaluation of Oligo(VDM) as a Crosslinker

The resulting copolymer solution was diluted to 33% solids by addition of more MEK. Two coating solutions were prepared: 1) a control containing no oligo(VDM) and 2) the test sample which contained oligo(VDM) prepared as in Example 3 in equal molar amount as the HEMA in the adhesive and ethanesulfonic acid [3 mol based on oligo(VDM)]. The solutions were knife-coated onto polyester film (0.05 mm) to a thickness of about 0.25 mm and dried in an air-circulating oven at 100° C. for 10 minutes to remove solvent and effect crosslinking; dry coating weights were about 64 g/m$^2$. Cohesive strengths of the resultant pressure sensitive tapes were compared by means of a standard shear strength test (Interim Federal Test Method Standard No. 147, Mar. 12, 1963), in which a 500 gram load was suspended from an adhesive contact area of 6.4 cm$^2$, and the time required for the tape to separate from the steel plate was measured and recorded in minutes as the average of three trials. The results are given in the following table:

| Sample | Shear (minutes) |
|---|---|
| Control | 24.7 |
| Test | 47.7 |

The data of this Example show the oligo(VDM)-containing formulation possessed a significantly increased cohesive strength relative to the control.

Various modifications and alterations of this invention will become apparent to those skilled in the art without departing from the scope and spirit of this invention, and it should be understood that this invention is not to be unduly limited to the illustrative embodiments set forth herein.

We claim:

1. A method comprising the steps:
 oligomerizing at least one 2-alkenyl 4,4-disubstituted azlactone in the presence of a catalytically effective amount of an acid to provide an oligomer having 2 to 15 units which are at least 30 mol % 2-alkenyl group polymerized units.

2. The method according to claim 1 wherein said acid is a Bronsted or Lewis acid.

3. The method according to claim 2 wherein said Bronsted acid has a pKa of less than 1.2.

4. The method according to claim 2 wherein said Bronsted acid is selected from the group consisting of: sulfuric acid, hydrogen chloride, hydrogen bromide, hydrogen iodide, trifluoroacetic acid, trichloroacetic acid, trifluoromethanesulfonic acid, p-toluenesulfonic acid, perchloric acid, and ethanesulfonic acid.

5. The method according to claim 2 wherein said Lewis acid is selected from the group consisting of: aluminum chloride, zinc chloride, boron trifluoride, antimony pentachloride, titanium tetrachloride and iodine.

6. The method according to claim 1 wherein said 2-alkenyl azlactone is selected from the group consisting of:
 2-vinyl-4,4-dimethyl-2-oxazolin-5-one,
 2-isopropenyl-4,4-dimethyl-2-oxazolin-5-one,
 2-vinyl-4-ethyl-4-methyl-2-oxazolin-5-one,
 2-vinyl-4,4-dimethyl-1,3-oxazin-6-one.

7. The method according to claim 6 wherein said 2-alkenyl azlactone is 2-vinyl-4,4-dimethyl azlactone.

* * * * *